United States Patent
Bonin et al.

[11] Patent Number: 5,943,130
[45] Date of Patent: Aug. 24, 1999

[54] IN SITU SENSOR FOR NEAR WAFER PARTICLE MONITORING IN SEMICONDUCTOR DEVICE MANUFACTURING EQUIPMENT

[75] Inventors: Michel P. Bonin, Livermore; Donald J. Holve, Danville, both of Calif.

[73] Assignee: Insitec, Inc., San Ramon, Calif.

[21] Appl. No.: 08/735,383

[22] Filed: Oct. 21, 1996

[51] Int. Cl.[6] ............ G01N 21/88; G01N 15/02
[52] U.S. Cl. ............ 356/336; 356/237.5; 356/338; 356/342
[58] Field of Search ............ 356/336, 338, 356/342, 237

[56] References Cited

U.S. PATENT DOCUMENTS

| | | | |
|---|---|---|---|
| 4,871,251 | 10/1989 | Preikschat et al. | 356/336 |
| 5,192,870 | 3/1993 | Batchelder et al. | 250/574 |
| 5,237,454 | 8/1993 | Snyder | 359/602 |
| 5,255,089 | 10/1993 | Dybas et al. | 358/101 |
| 5,294,806 | 3/1994 | Batchelder et al. | 250/574 |
| 5,316,983 | 5/1994 | Fujimori et al. | 356/336 |
| 5,528,360 | 6/1996 | Kohno | 356/237 |

*Primary Examiner*—Frank G. Font
*Assistant Examiner*—Zandra V. Smith
*Attorney, Agent, or Firm*—Skjerven, Morrill, MacPherson, Franklin & Friel LLP; David T. Millers

[57] ABSTRACT

A particle sensor for a semiconductor device fabrication tool scans a laser beam through a measurement volume immediately adjacent a wafer during processing and detects light scattered by particles adjacent the wafer. Scanning provides a real-time count of particles without interfering with processing. Detected light can be forward-scattered, side-scattered, or back-scattered depending on available optical access for a detector portion of the sensor. A pulse in the intensity of scattered light results each time a particle is scanned. Because the scanning velocity is high relative to the particle velocity, each particle may be scanned several times while the particle is in the measurement volume. Analysis fits a series of pulses observed for a single particle to a Gaussian distribution to determine a size, position, and velocity for each particle and a time-resolved particle count of the particles. The detected positions of particles are stored for targeting subsequent surface scans of wafers to detect defects.

39 Claims, 4 Drawing Sheets

IN SITU SENSOR FOR NEAR WAFER PARTICLE MONITORING IN SEMICONDUCTOR DEVICE MANUFACTURING EQUIPMENT

BACKGROUND OF THE INVENTION

1. Field of the Invention

This invention relates to particle sensors and particularly to particle sensors that use optical scanning and detection of scattered light.

2. Description of Related Art

Particle contaminants in semiconductor fabrication equipment such as plasma etch and vapor deposition chambers can deposit on semiconductor wafer surfaces and cause manufacturing defects that reduce the yield of operable devices. Great care is therefore taken to avoid particle contamination in such equipment. Even so, processing a batch of devices can create particles that cause defects in subsequent batches, and physical maintenance (or cleaning) of the equipment is periodically performed to reduce or eliminate these contaminants. Ideally, physical maintenance is only performed when needed to prevent the defect rate from reaching an undesirable level. If physical maintenance is too frequent, down time increases which reduces the total number of devices produced.

Physical maintenance can be scheduled according to the number of batches processed where the number of batches between scheduled maintenance is fixed and corresponds to a particular probability of the defect rate being unacceptably high. However, with this approach, physical maintenance at fixed intervals could be performed before cleaning is required which unnecessarily increases down time. At other times the physical maintenance may be too infrequent resulting in batches having unacceptable defect rates. Alternatively, physical maintenance may be initiated when device testing or wafer surface evaluation identifies an increased defect rate. However, several batches with high defect rates may be produced before test results are known. Another technique initiates physical maintenance when particle counts in a pump-line of the equipment become high. The primary disadvantage of this technique is that pump-line particle counts may not correlate with the defect rates at the wafer surface. This could potentially lead to inaccurate indications of physical maintenance requirements.

An improved technique would detect particles near the surface of a wafer during processing. This necessitates a particle sensor that can cope with the environment inside a reaction chamber and not disturb the manufacturing process. The particle sensor must detect particles less than a micrometer in diameter in close proximity to a wafer, possibly in the presence of a plasma, and should sample a relatively large volume near the surface of the wafer because the particle distribution may not be uniform across the surface of a wafer during processing and because the particle concentration is typically low near the wafer surface. Additionally, to provide maximum utility to the user, the sensor should provide particle size, particle velocity, and particle location information for each particle detected. Before the present invention, a particle sensor which met all of these requirements for in situ detection of particles during semiconductor manufacture was not available.

SUMMARY OF THE INVENTION

In accordance with the invention, a particle sensor detects particles immediately adjacent to a wafer during processing. The particle sensor scans a laser beam across a volume immediately adjacent to the wafer and detects light scattered when the beam encounters a particle. A detector measures the intensity of a portion of the light scattered from particles in a measurement volume formed by the intersection of the scanned volume and the real image of the detector. The intensity is then analyzed to determine the physical properties of each particle encountered. Optical systems which control the scan beam and detect scattered light are optimized for maximum suppression and rejection of stray light. This optimization is important to achieving acceptable signal-to-noise ratio in the detected signal.

Since the scan velocity of the laser beam is high compared to the typical speed of a particle in the measurement volume, a typical particle causes several pulses of scattered light while in the measurement volume. The multiple pulses improve statistical and measurement accuracy when compared with single pulse detection. Analysis of a series of scattered light pulses originating from a single particle can determine the diameter, position, and velocity of the particle. The duration of each pulse for a particle indicates a radial coordinate of the particle. The timing of the pulses relative to the limits of the scan range indicate an angular coordinate of the particle. The radial and angular information can be combined with information indicating the position of a scanner mirror to determine the position of the particle in the measurement volume. The speed of the particle along an axis perpendicular to the scan plane can be determined from the collection of peak intensities that constitute a single particle scattering event. These peak intensities are typically proportional to the intensity of the section (top, middle, or bottom) of the scan beam scattered by the particle. Accordingly, the evolution of the peak intensities indicates the progress and velocity of the particle across the diameter of the scan beam. Particle velocity or speed in a direction normal to the scan plane is determined from the best fit to the peak intensities that constitute a scattering event. This fit is typically a Gaussian distribution characteristic of the scan beam's radial intensity distribution. Fitting to a distribution reduces the influence of light and electronic noise in an individual measurement.

In one embodiment, a particle sensor includes a scanner, a detector, and a signal processor. The scanner sweeps a beam of light across a measurement volume, and may include a laser and a scanning mirror that generate and direct the beam into the measurement volume inside a reaction chamber. The detector collects scattered light and generates a signal that indicates the intensity of light scattered in a particular direction from the measurement volume. The detector may be positioned to detect back-scattered, side-scattered, or forward-scattered light.

To isolate the desired scattered light from background light, the detector includes an optical system which focuses light from the measurement volume through an aperture of a photodetector. Light from outside the measurement volume is not sharply focused through the aperture and is reduced relative to the desired scattered light. Bandpass filters selective to the wavelength of light from the scan beam further reduce background relative to the desired signal. Optionally, a beam dump absorbs the non-scattered portion of the scan beam to reduce stray reflections that may otherwise increase background light at the scan beam's wavelength.

A variety of different configurations may be used when incorporating the particle sensor as part of semiconductor fabrication tool. For example, one or more detectors can be mounted at different locations on a reaction chamber to detect back-scattered, side-scattered, or forward-scattered light, and a mirror and/or other optical elements can be employed to reflect the scan beam so that a detector mounted adjacent the scanner detects forward-scattered light.

Electronic filtering and analysis of the signal from a detector determines the size, position, and velocity of the detected particle. The detection and measurement of defect causing particles provide an accurate, real-time indication of defect rates for more efficient management of semiconductor fabrication tools. The information from the particle sensor, particularly the position of defect causing particles relative to the wafer, can be used to target subsequent surface scans for defects on the wafer. Thus, the particle sensor improves detection of defects early in the manufacturing process.

BRIEF DESCRIPTION OF THE DRAWINGS

Use of the same reference symbols in different figures indicates similar or identical items.

DETAILED DESCRIPTION OF THE PREFERRED EMBODIMENTS

In accordance with an embodiment of the invention, a particle sensor scans a measurement volume with a laser beam that passes immediately adjacent to a wafer surface inside a semiconductor fabrication tool during processing. Through scanning, the beam samples a relatively large measurement volume, one or more cm in width, just above the surface of the wafer without interfering with the fabrication process. A detector collects back-scattered, side-scattered, or forward-scattered light from the measurement volume to detect the presence of a particle in the measurement volume. The light collection geometry is primarily determined by the available optical access of the semiconductor fabrication tool. A signal from the detector that indicates the intensity of light at the wavelength of the scan beam is analyzed to remove background noise and count individual particles to approximately 0.15 micrometer in diameter. The sizes, positions, and velocities of the particles detected within the measurement volume can also be determined.

Figure 1:
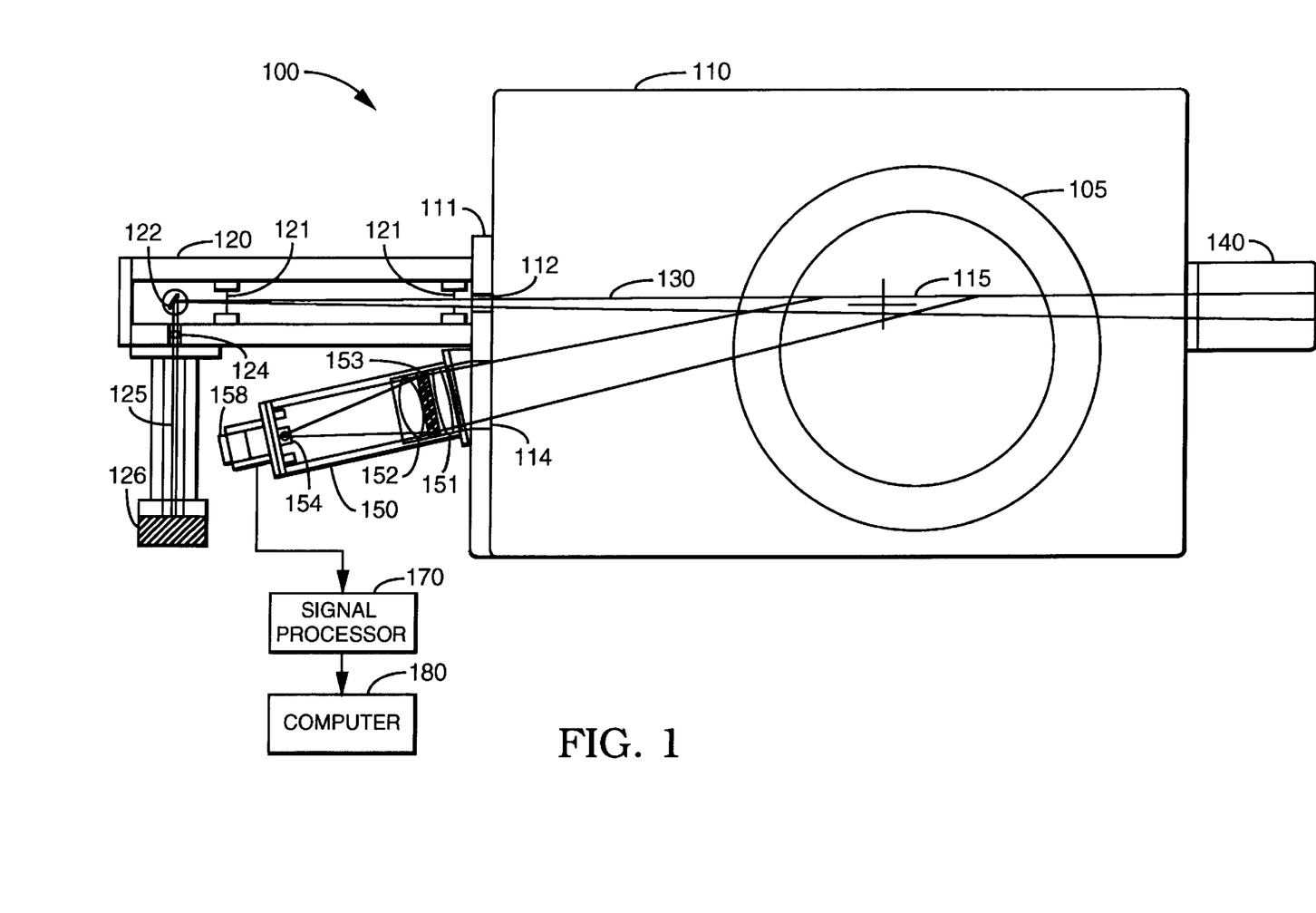
FIG. 1 shows an in situ particle sensor in accordance with an embodiment of the invention.

FIG. 1 shows a semiconductor fabrication tool 100 having a reaction chamber 110 and an attached particle sensor in accordance with an embodiment of the invention. The particle sensor includes a transmitter 120 that scans a laser beam 130 across a measurement volume 115 adjacent to a surface of a wafer 105 in reaction chamber 110 and a detector 150 that collects light which is scattered by particles in measurement volume 115. In accordance with an aspect of the invention, scanning of laser beam 130 makes measurement volume 115 large when compared to the size of particles detected. In particular, the size of measurement volume 115 depends on the range of motion of beam 130, the diameter of beam 130, and the size of an aperture 154 in detector 150. In accordance with another aspect of the invention, particles are counted adjacent to the wafer 105 without interfering with processing because transmitter 120 and detector 150 are mounted on the walls of reaction chamber 110 and are away from wafer 105.

In transmitter 120, a laser 126 produces laser beam 130 that a scanning mirror 122 directs into reaction chamber 110. Laser beam 130, which is also referred to herein as scan beam 130, has a characteristic wavelength (or wavelengths) selected to minimize confusion with background light that may be generated in reaction chamber 110. Common sources of background light include a plasma for plasma-based processes and thermal induced background light (or blackbody radiation) in processes operating at high temperatures. In an exemplary embodiment of the invention, laser 126 is a high powered laser diode having a short wavelength, for example, between about 480 nm and 670 nm, or alternatively, a 70 mW, air-cooled Argon-Ion laser having a wavelength of 488 nm. Light from laser 126 can be used collimated (i.e. as parallel rays) or focussed, depending on the particle size of interest.

In the exemplary embodiment, a laser beam from laser 126 is directed onto to a focusing lens 124. The focal length of lens 124 is selected so that scan beam 130 is focussed near the center of measurement volume 115. In the exemplary embodiment, focussing lens 124 is a Newport Optical KPX094, which is a 25.1 mm diameter, $MgF_2$ coated, plano-convex lens having a focal length of 100 mm for 488 nm light. Alternatively, an achromat would be used if a more accurately defined focus is required.

Oscillating motion of mirror 122 sweeps scan beam 130 back and forth through measurement volume 115. An operating parameter of drive electronics for mirror 122 controls the range of motion of scanning mirror 122 and thereby controls one dimension of measurement volume 115. In the exemplary embodiment, mirror 122 is a resonant scanning mirror having a ±15° maximum range of motion and an oscillation frequency of 4 KHz. A model CRS4 counter rotating, resonant scanner available from General Scanning, Inc. with a GSI CRS driver board is suitable for scanning mirror 122. A rotating scanner could also be used in an alternative embodiment in applications where the service life of a resonant scanner is unacceptable. Scanning mirror 122 directs laser light through baffles 121 which are made of an absorptive material such as flat-black painted aluminum to absorb stray light not directed within the desired angular scanning range.

Scan beam 130 enters reaction chamber 110 through a vacuum sealed optical window 112 in a wall of reaction chamber 110. Alternatively, window 112 is replaced by an opening that exposes the interior of transmitter 120 to the environment in reaction chamber 110. In an embodiment where window 112 is replaced by an opening, transmitter 120 is vacuum sealed to maintain the desired gases in reaction chamber 110, and components inside transmitter 120 must withstand exposure to the reactants from reaction chamber 110. With window 112, the components of transmitter 120 do not require the same level of durability, but window 112 may scatter light from beam 130 and increase background light in reaction chamber 110. This increase in background light has the undesirable effect of increasing the minimum detectable particle size. To suppress stray light generation by window 112, an aperture can be installed at or near the interior surface of window 112.

A beam dump 140 reduces background light by absorbing from light beam 130 light that passes through measurement volume 115 without significant deflection. Beam dump 140 has an open aperture through which the unscattered portion of beam 130 enters and an interior geometry that is generally configured for maximum absorption of the unscattered portion of beam 130. However, optimizing the angular arrangement of the exterior of beam dump 140 is critical to minimization of stray light collected at detector 150. Specifically, the external geometry should be such that light entering chamber 110 from transmitter 120 cannot directly reflect off of the exterior of beam dump 140 and into detector 150. For additional reductions in stray light detected, the field of view of collection optics for detector 150 should not include the open aperture of beam dump 140. In alternative embodiments, beam dump 140 can be mounted inside or outside reaction chamber 110 or can be eliminated when background light is not critical, for example, when only larger particles are detected or where light scattered from the walls of reaction chamber 110 is unlikely to reach detector 150.

Some of the light in scan beam 130 which strikes a particle in measurement volume 115 is scattered into detector 150 which measures the intensity of the scattered light. No assumptions are made or required regarding the coherent nature of the scattered light relative to scan beam 130. Detector 150 can include a recessed optical window 114 which is vacuum sealed to protect optical elements (lenses 151 and 152, a bandpass filter 153, and aperture 154) from the environment in reaction chamber 110. Alternatively, if a window in reaction chamber 110 is suitably positioned, a separate window for detector 150 is not necessary. Lenses 151 and 152 focus light that enters detector 150 through window 114. In particular, light originating from measurement volume 115 is sharply focused through aperture 154 into a photodetector 158. Background light that a plasma in reaction chamber 110 may generate or which may be scattered from beam 130 outside measurement volume 115 also passes through optical window 114 but little of the background light is focused onto the input of photodetector 158. The intensity of such background light is therefore reduced relative to light scattered in measurement volume 115.

The diameter of lenses 151 and 152 are selected to match the diameter of window 114, and the focal lengths of lenses 151 and 152 are primarily selected according to the distance from detector 150 to measurement volume 115 and the available space in detector 150. In the exemplary embodiment, lens 151 is Newport Optical PACO79 which is a 38.1 mm diameter, $MgF_2$ coated achromat having a focal length of 250 mm; and lens 152 is a Newport Optical PACO70 which is a 38.1 mm diameter achromat having a focal length of 76.2 mm.

Bandpass filter 153 is between lenses 151 and 152 and further reduces background light by removing light at wavelengths other than the characteristic wavelength of scan beam 130. In the exemplary embodiment where light in scan beam 130 has a wavelength of 488 nm, filter 153 is a 488 BP5 interference filter from Omega Optical and blocks light having a wavelength that differs from 488 nm by more than about ±3 nm. For applications where background light levels are low, the bandwidth of filter 153 can be increased to about 7 nm or more. Increasing the bandwidth to 7 nm increases transmission to about 50% of the incident light at the desired wavelength.

Aperture 154 controls a dimension of measurement volume 115. In the exemplary embodiment, aperture 154 is a slit about 3 mm in width. Other size or geometry apertures may be used to provide larger or smaller measurement volumes.

Photodetector 158, which may be a conventional photomultiplier tube such as a Hamamatsu R5600U, generates an analog signal indicating the intensity of the light collected and provides the signal to a signal processor 170. Signal processor 170 includes a bandpass filter which removes electronic noise having frequency above 1 MHz or below about 100 Hz. Signal processor 170 also identifies scattering events and provides to computer 180 digital information describing the peaks, widths, and timing of pulses in the analog signal. Computer 180, which may be an IBM-compatible 486 or more powerful computer, executes software which analyzes the information from signal processor 170 to determine the size, position, and velocity of particles within measurement volume 115. Exemplary analysis is further described below.

In the embodiment of FIG. 1, transmitter 120 and detector 150 are mounted on a support frame 111 that directly attaches to a wall of reaction chamber 110. With transmitter 120 and detector 150 adjacent each other, detector 150 collects light that is nearly back-scattered in measurement volume 115. Alternatively, detector 150 can be mounted separately on another wall of reaction chamber 110 to detect side-scattered or forward-scattered light from measurement volume 115. As a further alternative, more than one detector 150 per transmitter 120 can provide multiple measurements.

Figure 2:
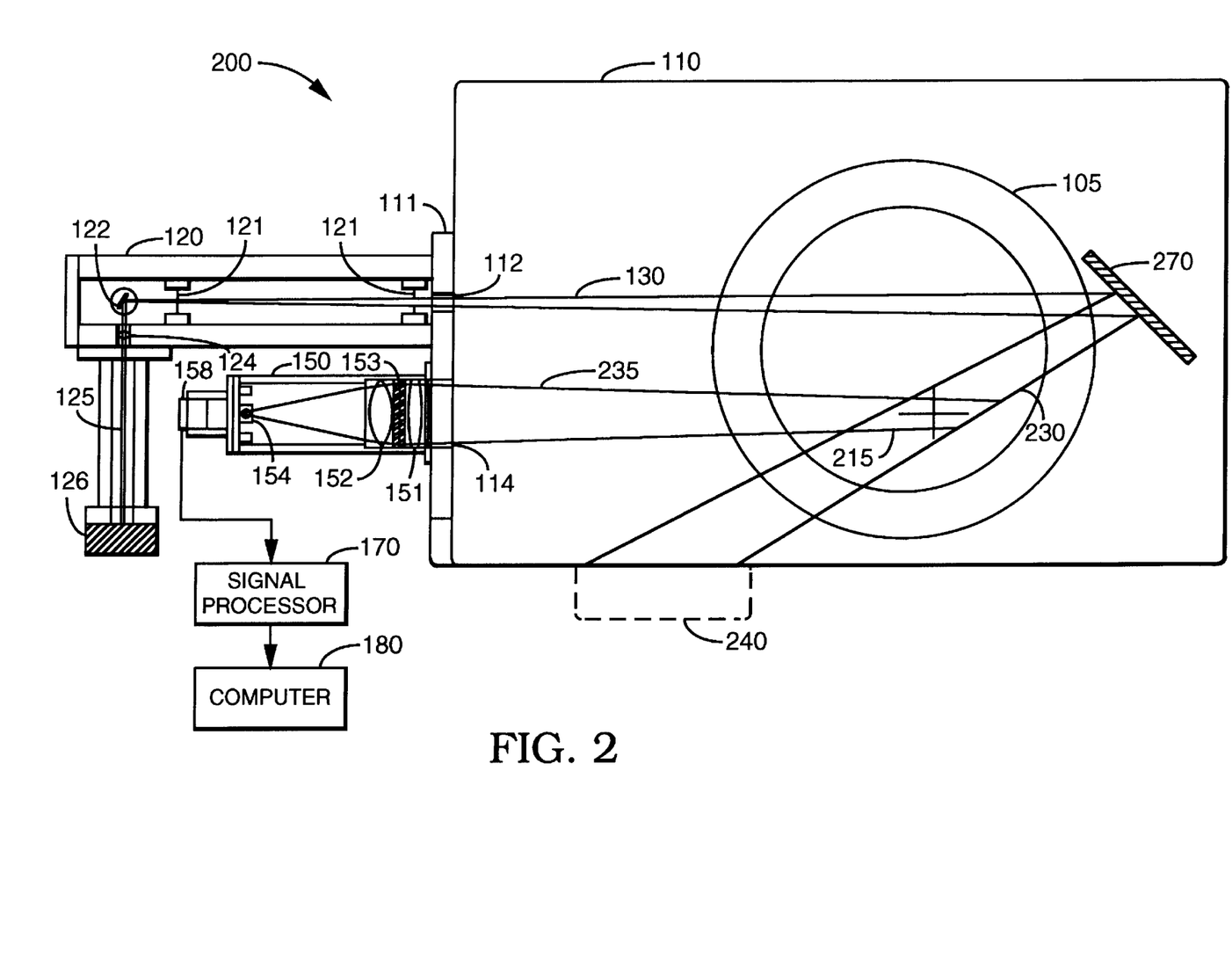
FIG. 2 shows an in situ particle sensor in accordance with another embodiment of the invention.

FIG. 2 shows an embodiment of a fabrication tool 200 where detector 150, although mounted adjacent transmitter 120, measures light which is nearly forward-scattered (i.e. at an angle of about 5° to 10°) from a measurement volume 215. The elements of fabrication tool 200 which are similar or identical to those described above in regard to FIG. 1 are identified by the same reference symbols as used in FIG. 1, and the above description of those elements also applies here.

Fabrication tool 200 differs from fabrication tool 100 primarily in the addition of a mirror 270 within reaction chamber 110. Mirror 270 reflects scan beam 130 towards measurement volume 215 which is within the focus of detector 150. The focal lengths of lenses 124 and 151 are adjusted to accommodate measurement volume 215 in FIG. 2 being in a different location from measurement volume 115 in FIG. 1, and detector 150 is mounted at a different angle so that the optical axis of detector 150 passes through measurement volume 215.

An advantage of the geometry shown in FIG. 2 is that detector 150 collects scattered light 235 which is at relatively small angles with reflected scan beam 230. Small angle scattering typically provides a higher signal-to-noise ratio than does back-scattering because the intensity of forward-scattered light is more than an order of magnitude higher than the intensity of back-scattered light for nearly any light wavelength and particle diameters between 0.2 $\mu$m and 10 $\mu$m. A beam dump 240, if used, is repositioned according to the direction of unscattered light and should have internal and external surfaces that meet the same requirements as described above for beam dump 140 of FIG. 1. A beam dump may not be required for the geometry of the particle sensor in fabrication tool 200 because of the higher signal level of forward-scattered light.

Photodetector 158 generates an analog signal indicating the intensity of collected light at the scan-beam wavelength. Background light in reaction chamber 110 causes the analog signal to have a DC background level with relatively small fluctuations. When a particle passes through measurement volume 115, the interaction of the particle and scan beam 130 generates a series of pulses in the signal that rise above the background. The electronic bandpass filter in signal processor 170 removes the DC background component of the analog signal.

Figure 3:
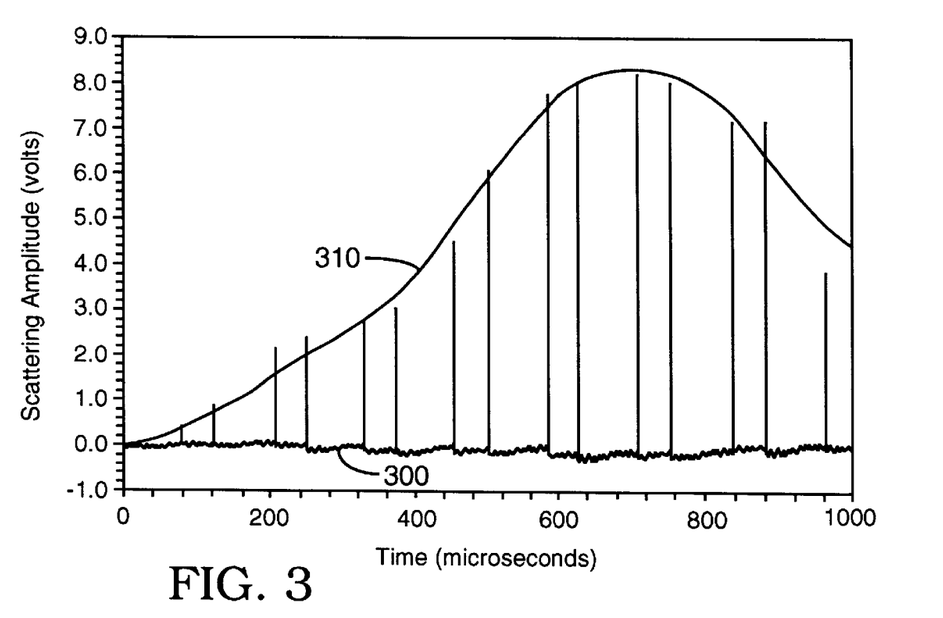
FIGS. 3, 4, and 5 show plots of typical scattered light intensities created by particles passing through the measurement volumes of particle sensors such as illustrated in FIGS. 1 and 2.
Figure 4:
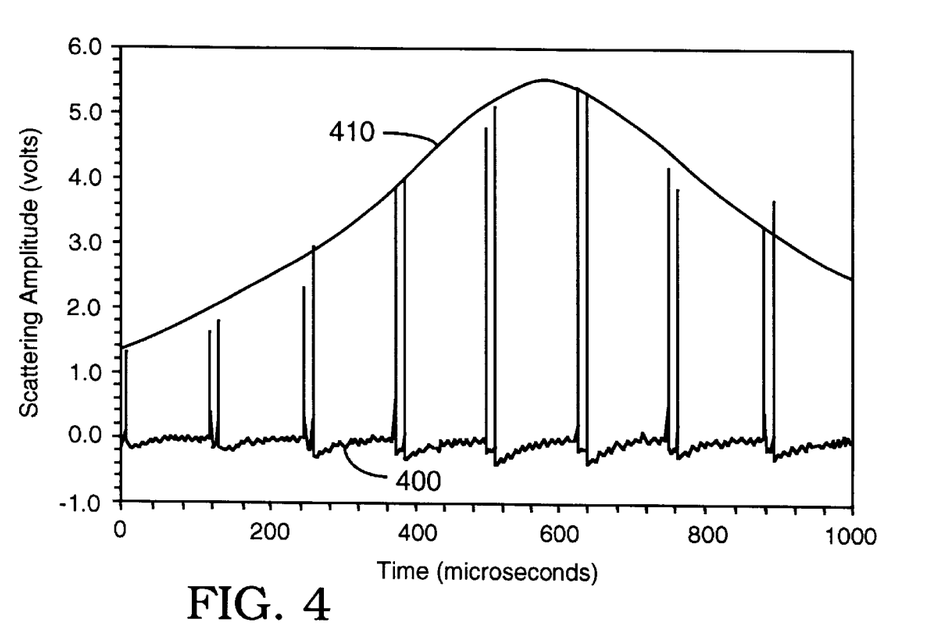
Figure 5:
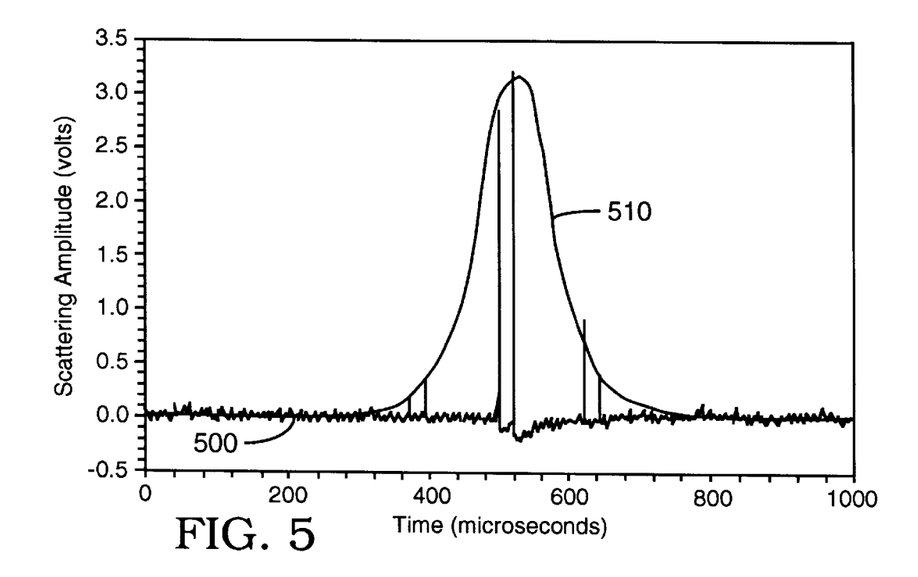

FIGS. 3, 4, and 5, respectively, show exemplary signals 300, 400, and 500 that result from filtering the analog signal from photodetector 158. Signals 300, 400, and 500 are characteristic of back-scattering from a 0.8 $\mu$m particle in a reaction chamber without any manufacturing processes taking place. The signal-to-noise ratio (SNR) for each pulse from a 0.8 $\mu$m particle is quite high. The SNR would be lower for a smaller particle that scatters less light and causes a weaker signal. Additionally, processes in the reaction chamber can potentially increase light and electronic noise, making small particle detection more difficult.

Scattered light from measurement volume 115 causes a signal pulse each time scan beam 130 illuminates a detectable particle. In the exemplary embodiment, the velocity of scan beam 130 in measurement area 115 is much higher than typical particle velocities, and a particle is illuminated by more than one sweep of beam 130 as the particle passes through measurement volume 115. Accordingly, a typical particle passing through measurement volume 115 results in a scattering event including multiple illuminations of the particle and multiple pulses where one pulse occurs each time scan beam 130 reverses direction. Signal 300 of FIG. 3 illustrates a signal for a portion of a typical single particle scattering event. The signature characteristics of a single particle scattering event reduce or eliminate false particle counting since events that do not exhibit multiple-pulse signatures can be screened from the count.

The time between pulses indicates the angular position of a particle relative to the limits of the scan range. If the particle is near one limit of the scan range, the time required for scan beam 130 to scan from the particle to the near limit and back is shorter than the time required for scan beam 130 to scan from the particle to the far limit and back. Thus, a particle being close to an edge of measurement volume 115 results in pairs of pulses being closely spaced. FIG. 4 shows a signal 400 generated for a particle that is relatively close to one edge of measurement volume 115. Pulses are equally spaced if the particle is in the middle of measurement volume 115. Thus, the location of the particle along the scan direction can be determined from the time separation of pulses. Theoretically, the speed of a particle along the scan direction can be determined from changes in separation between consecutive pairs of pulses. However, changes in this separation are on the order of the diameter of scan beam 130 divided by the scan velocity and are difficult to measure.

Each pulse has a profile that is characteristic of the intensity profile of scattering beam 130 and of the scattering properties of the particle. In the exemplary embodiment, scattering beam 130 has a Gaussian intensity profile that causes each pulse for a particle to also be Gaussian. The peaks of a series of pulses for a particle also follow the Gaussian distribution of the beam profile as the particle enters, passes through, and exits from measurement volume 115. FIG. 3 does not have sufficient time resolution to demonstrate the Gaussian shape of individual pulses but does show a Gaussian distribution 310 fit to the peaks of pulses in signal 300.

Figure 6:
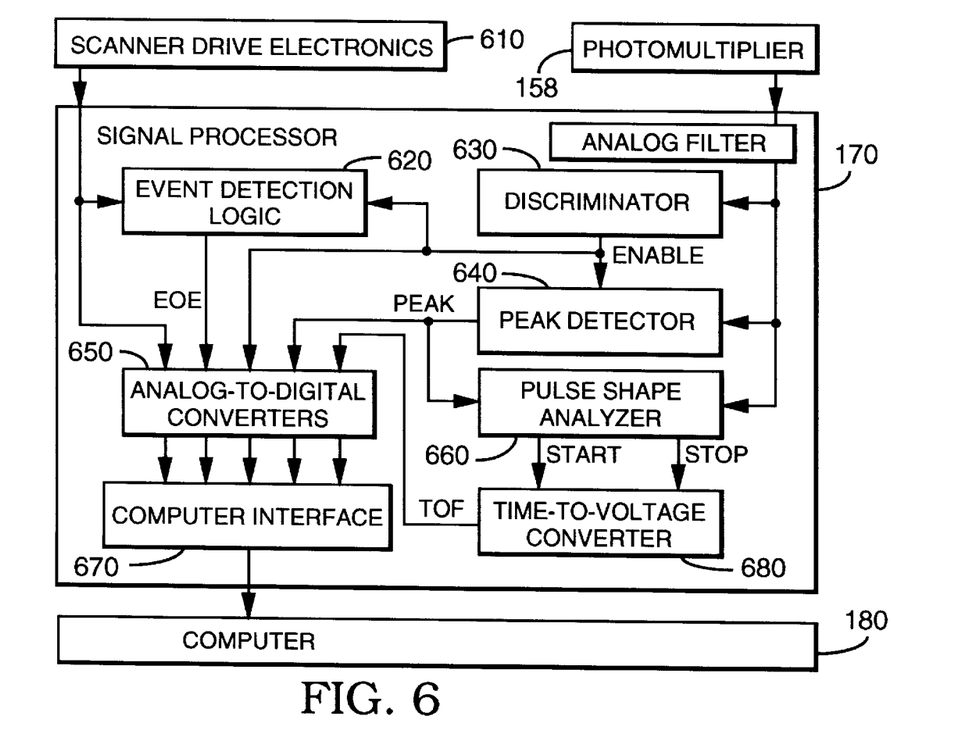
FIG. 6 is a block diagram of an electronic system for the particle sensor of FIG. 1 or 2.

Signal processor 170 detects each pulse, determines the peak amplitude for each pulse, determines the width (i.e. duration) of a portion of each pulse, and identifies the ends of scattering events. FIG. 6 shows a block diagram of an embodiment of signal processor 170. For signal analysis, a discriminator 630 in signal processor 170 is set at a level above the background in the analog signal from photodetector 158. Discriminator 630 is a level-triggered device that detects a pulse when the analog signal rises above a programmable level. Upon detecting a pulse, discriminator 630 generates a signal to a computer interface 670, a peak detector 640, and event detection logic 620. Computer interface 670 sends an interrupt to computer 180 for each pulse detected, and computer 180 notes the time of each interrupt as the time of a pulse. At the interrupt for a first peak detected in a scattering event, a clock on the signal processor interface card is started. A time from the clock is read and transferred to computer 180 each time a new peak is detected. The interrupt from signal processor 170 to computer 180 is given priority over all other overhead in the system to ensure that no scattering events are missed.

For each pulse, signal processor 170 sends to computer 180 information indicating the peak amplitude of the pulse, the duration of the pulse, and the direction of motion of scan beam 130 when the pulse occurred. To determine the peak amplitude of a pulse, discriminator 630 activates peak detector 640 that detects and holds the peak voltage of the analog signal. Analog-to-digital converters (ADCs) 650 convert this peak voltage to a digital value that computer interface 670 sends to computer 180. Peak detectors for analog signals are well known and available commercially from a variety of sources.

To determine the duration of each pulse, a pulse shape analyzer 660 coupled to peak detector 640 identifies points on the trailing edge of each pulse that are 80% and 60% of the peak voltage of the pulse. Pulse shape analyzer 660 starts and stops a time-to-amplitude converter 680 at these points so that a voltage TOF from converter 680 is proportional to the time between 80% and 60% points. Voltage TOF is also proportional to the "time of flight" of the particle through scan beam 130 since the time to cross between the 80% and 60% points of a Gaussian distribution (scan beam 130) is a fixed percentage of the total time required for scan beam 130 to sweep past the particle. ADCs 650 convert voltage TOF to a digital value that computer interface 670 provides to computer 180.

A PCSV single particle counting signal processor available from Insitec Measurement Systems, Inc. implements the functions of discriminator 630, peak detector 640, pulse analyzer 660, time-to-voltage converter 680, ADCs 650, and computer interface 670. Signal processor 170 additionally identifies the scan direction for scan beam 130 and determines the end of a series of pulses associated with a single particle scattering event. In the exemplary embodiment, drive electronics 610 for transmitter 120 generates a square wave signal where the level of the square wave signal indicates the direction of motion of mirror 122 and scan beam 130. From the square wave signal, ADCs 650 and computer interface 670 provide to computer 180 a bit indicating the level of the square wave when a pulse is detected. Event detection logic 620 is coupled to discriminator 630 and drive electronics 610 and identifies the end of a scattering event. When discriminator 630 fails to detect a pulse within a half period of the square wave signal from drive electronics 610, event detection logic 620 sends an end of event signal EOE to computer 180 via computer interface 670.

Assuming no additional interrupts are received after the end of event signal, computer 180 processes the information from all of the pulses in the scattering event to determine a radial position, an angular position, a radial velocity component, and a velocity component perpendicular to the scan plane for a particle that caused the just ended scattering event. Computer 180 uses the "time of flight" values to determine the radial position, relative to scan mirror 122, of the particle. For the pulses having the highest peak amplitude, the center portion of scan beam 130 sweeps across the particle; and relative to scan beam 130, the particle moves across a diameter of scan beam 130. Accordingly, the speed of scan beam 130 relative to the particle is approximately equal to the width of scan beam 130 divided by the time of flight. Since the velocity of scan beam 130 is large compared to the velocity of the particle, the relative speed is also about equal to the product of the radial distance (i.e. the distance between the particle and the rotation axis of scanning mirror 122) and the angular velocity of scan beam 130 about the rotation axis. The radial distance to the particle is thus determined from the width of scan beam 130 divided by the time of flight and the angular velocity of scan beam 130. The radial velocity of the particle is determined from the change in radial positions between two pulses divided by the time between the pulses.

Computer 180 determines the angular (or circumferential) position of the particle from the scanner state and the time between consecutive pulses. In particular, the angular distance from an edge of measurement volume 115 is equal to the product of the angular velocity of scan beam 130 and half the time between consecutive pulses. The base edge for angular distance measurement is determined from the scan direction which is in turn determined from the output of scanner drive electronics 610.

The angular and radial position of the detected particle identifies a point on wafer 105 that may contain a defect caused by the particle. In accordance with an aspect of the invention, the identified position for the particle can be targeted for examination during surface scanning of wafer 105. This improves the probability of early detection of defects during manufacture.

To determine a particle's size and velocity perpendicular to the scan plane, computer 180 fits a Gaussian distribution to the peaks of the individual pulses. FIGS. 3, 4, and 5 show Gaussian fits 310, 410, and 510 for signals 300, 400, and 500 respectively. The maximum of the Gaussian fit can be mapped to a particle diameter using a calibrated response function that correlates particle diameter with scattered light intensity. In particular, well known Mie scattering theory provides a relationship between particle size and the intensity of scattered light. Such relationships between scattered light intensity and particle size are described, for example, by: Holve, D. J. "Optical Particle Sizing for in situ measurements—Part 1," Applied Optics, 18(10):1632 (1979); Holve, D. J. "Optical Particle Sizing for in situ measurements —Part 2," Applied Optics, 18(10):1646 (1979); and Mie, G.: Ann. d. Physik, 30(4) 377 (1908). The theoretical relationship between scattered intensity and particle size primarily depends on: 1) relative input intensity; 2) light scattering geometry; 3) laser illumination wavelength; and 4) particle refractive index. The light scattering geometry and laser wavelength are constant for a particular system. Calibration using particles having known diameters shifts or fits the theoretical curve relating particle size and normalized intensity to the empirically determined peaks of Gaussian fits for the particles of known diameter.

Correct calibration of the particle sensor depends on the scan beam intensity being fixed. However, the effective beam intensity can change because of window fouling after the last cleaning. To monitor these changes, output of one or more beam power diodes can be read at the start of each measurement. A beam power diode (or detector) can be located, for example, in transmitter 120 adjacent scan beam 130 where the beam power diode detects light scattered from window 112 or in the path of unscattered light in a forward scattering geometry. The amount of light detected by the beam power diode changes with window fouling. In particular, readings from a beam power diode in transmitter 120 increase and readings from a beam power diode in the path of unscattered light decrease as window 112 becomes more fouled. A relation between readings from a beam power diode and beam intensity can be determined empirically. Based on the readings, computer 180 determines whether the effective intensity has changed from a baseline value. In one embodiment of the invention, computer 180 controls the power output from laser 126 and/or the excitation voltage of photomultiplier 158 and compensates for changes in effective intensity.

The interval between points on the Gaussian fit which are 13% ($1/e^2$) of the maximum is the time required for the particle to move a distance equal to the waist diameter of scan beam 130 along an axis normal to the scan plane. (The waist diameter is the diameter at which the beam intensity has fallen to about 13% ($1/e^2$) of its maximum intensity.) Computer 180 divides the $1/e^2$ beam diameter by that time to determine a component of the particle's velocity perpendicular to the scan plane. FIG. 5 shows a signal 500 having a narrow Gaussian fit 510 resulting from a particle traversing measurement volume 115 at a speed higher than that of the particles causing signals 300 and 400 in FIGS. 3 and 4, respectively.

Although the invention has been described with reference to particular embodiments, the description is only an example of the invention's application and should not be taken as a limitation. In particular, even though much of preceding discussion was aimed at detectors using a single scan beam, alternative embodiments of this invention include use of multiple scan beams, and multiple detectors multiplexed to a common scanner and a single signal processor. Various other adaptations and combinations of features of the embodiments disclosed are within the scope of the present invention as defined by the following claims.

We claim:

1. A particle sensor comprising:
   a transmitter that sweeps a beam of light across a measurement volume;
   a detector comprising a photodetector and an optical system that collects light scattered from the measurement volume and directs that light into the photodetector, wherein the photodetector generates a signal indicating an intensity of the light directed into the photodetector; and
   a processor coupled to analyze a signal from the photodetector, the processor comprising:
   a pulse detector that detects pulses in the signal from the photodetector; and
   an event detector that identifies a series of the pulses that corresponds to a particle and results from the particle scattering light from multiple sweeps of the beam while the particle moves through the measurement volume.

2. The particle sensor of claim 1, wherein the optical system comprises a stop defining an aperture through which light must pass to reach the photodetector, and a lens system that focuses light from a measurement volume into the aperture.

3. The particle sensor of claim 2, wherein the lens system comprises a first lens having a first focal point within the measurement volume and a second lens having a second focal point within the aperture.

4. The particle sensor of claim 2, wherein the optical system further comprises an optical bandpass filter that passes light having a wavelength equal to that of the beam.

5. The particle sensor of claim 1, further comprising a beam dump positioned to absorb light from the scan beam which traverses the measurement volume without being scattered.

6. The particle sensor of claim 5, wherein the beam dump has an exterior such that no light from the scan beam reflects directly from the exterior of the beam dump into the optical system.

7. The particle sensor of claim 5, wherein an aperture of the beam dump is outside a field of view of the optical system.

8. The particle sensor of claim 1, wherein the optical system comprises an optical bandpass filter that passes light having a wavelength equal to that of the beam.

9. The particle sensor of claim 1, wherein the transmitter comprises a laser that generates the beam and a scanning mirror positioned to reflect the beam into the measurement volume, the scanning mirror being movably mounted, wherein movement of the scanning mirror sweeps the beam across the measurement volume.

10. The particle sensor of claim 9, wherein the scanning mirror comprises a resonant scanning mirror.

11. The particle sensor of claim 9, wherein the scanning mirror comprises a rotating mirror.

12. The particle sensor of claim 9, wherein the transmitter further comprises a focusing lens having a focal length equal to an optical path length from the focusing lens to a point in the measurement volume.

13. The particle sensor of claim 1, wherein the measurement volume is immediately adjacent to a device being manufactured.

14. The sensor of claim 1, wherein the processor further comprises means for determining a velocity of the particle corresponding to the series of pulses.

15. The sensor of claim 1, wherein the processor further comprises means for determining a size for the particle corresponding to the series of pulses.

16. The sensor of claim 1, wherein the processor determines a property of a particle by processing information derived from multiple pulses that the event detector identifies as being in a series of pulses that corresponds to the particle.

17. The sensor of claim 16, wherein the property is size of the particle.

18. The sensor of claim 16, wherein the property is a velocity component of the particle.

19. The sensor of claim 16, wherein the property is a co-ordinate of position.

20. A particle detector comprising:
a transmitter that sweeps a beam of light across a measurement volume, wherein the transmitter comprises a drive circuit that controls movement of the beam;
a detector comprising a photodetector and an optical system that collects light scattered from the measurement volume and directs that light into the photodetector, wherein the photodetector generates a signal indicating an intensity of the light directed into the photodetector; and
a processor coupled to analyze a signal from the photodetector, wherein the processor comprises:
a discriminator coupled to the detector, wherein in response to the signal from the photodetector rising above a threshold level, the discriminator detects a pulse in the signal; and
event detection logic coupled to the discriminator and the drive circuit, the event detection logic detecting an end of a series of pulses caused by a particle in the measurement volume.

21. The particle detector of claim 20, wherein the processor further comprises a computer adapted to identify a size of a particle from information characterizing a series of pulses caused by the particle.

22. The particle detector of claim 21, wherein the computer further processes the information characterizing the series of pulses to determine a radial position and a circumferential position of the particle relative to the transmitter.

23. The particle detector of claim 21, wherein the computer determines the size of the particle by fitting peaks of the series of pulses to a distribution characteristic of the intensity of the beam, wherein a peak of the distribution indicates the size of the particle.

24. Semiconductor device fabrication equipment comprising:
a reaction chamber;
a transmitter that sweeps a beam of light across a measurement volume immediately adjacent to a device being manufactured inside the reaction chamber;
detector comprising a photodetector and an optical system that directs light scattered from the measurement volume into the photodetector, wherein the photodetector generates a signal that indicates intensity of the light directed into the detector, wherein the optical system in the detector is positioned to direct into the photodetector light that is forward-scattered from the measurement volume;
a processor coupled to analyze the signal from the detector; and
a mirror, wherein the detector is mounted adjacent to the transmitter and the mirror is positioned to reflect light from the transmitter to the measurement volume.

25. A fabrication process comprising:
scanning a beam through a measurement volume adjacent a work piece, while processing the work piece;
detecting light scattered from the measurement volume; and
analyzing evolution of an intensity of the light scattered to identify a particle in the measurement volume, wherein analyzing the evolution of the light intensity comprises:
separating pulses in the intensity from background noise in the intensity;
identifying a series of pulses corresponding to light scattered by a particle in the measurement volume; and
determining a size of the particle from the series of pulses.

26. The process of claim 25, wherein determining the particle size comprises fitting a distribution associated with an intensity profile of the beam to peak of the pulses in the series, and determining the size of the particle from the distribution fit to the peaks.

27. The process of claim 26, further comprising determining a velocity component for the particle from a width of the distribution fit to the peaks.

28. The process of claim 25, wherein the work piece is a semiconductor wafer.

29. A fabrication process comprising:
scanning a beam through a measurement volume adjacent a work piece, while processing the work piece;
detecting light scattered from the measurement volume; and
analyzing evolution of an intensity of the light scattered to identify a particle in the measurement volume, wherein analyzing the evolution of the light intensity comprises:

separating pulses in the intensity from background noise in the intensity;

identifying a first pulse corresponding to light that a particle in the measurement volume scatters when the beam scans in a first direction;

identifying a second pulse corresponding to light that the particle scatters when the beam scans in a second direction; and determining a circumferential position of the particle from the time interval between the first and second pulses.

30. The process of claim 29, wherein the workpiece is a semiconductor wafer.

31. A fabrication process comprising:

scanning a beam through a measurement volume adiacent a work piece, while processing the work piece;

detecting light scattered from the measurement volume; and analyzing evolution of an intensity of the light scattered to identify a particle in the measurement volume, wherein analyzing the evolution of the light intensity comprises:

separating a pulse in the intensity from background noise in the intensity;

measuring of a duration of at least a portion of the pulse; and determining a radial position of a particle from the duration of the pulse and an angular velocity of the beam.

32. The process of claim 31, wherein the workpiece is a semiconductor wafer.

33. A fabrication process comprising:

scanning a beam through a measurement volume adjacent a work piece, while processing the work piece;

detecting light scattered from the measurement volume;

analyzing evolution of an intensity of the light scattered to identify a particle in the measurement volume;

analyzing the intensity of the scattered light to identify an area on a surface of the work piece where a particle may deposit; and scanning the area on the surface of the work piece for defects.

34. The process of claim 33, wherein the workpiece is a semiconductor wafer.

35. Semiconductor device fabrication equipment comprising:

a reaction chamber;

a transmitter that directs a beam of light through a measurement volume adjacent to a device being manufactured inside the reaction chamber;

a detector including a photodetector and an optical system, the optical system configured to direct scattered light from the measurement volume into the photodetector and the photodetector configured to generate a signal defined by the scattered light; and a processor coupled to analyze the signal form the detector, the processor comprising:

a pulse detector detecting pulses in the signal from the detector; and an event detector detecting a series of pulses caused by a particle in the measurement volume.

36. The semiconductor device fabrication equipment of claim 35, wherein the optical system in the detector is positioned to direct into the photodetector light that is back-scattered from the measurement volume.

37. The semiconductor device fabrication equipment of claim 35, wherein the optical system in the detector is positioned to direct into the photodetector light that is side-scattered from the measurement volume.

38. The semiconductor device fabrication equipment of claim 35, wherein the optical system in the detector is positioned to direct into the photodetector light that is forward-scattered from the measurement volume.

39. The semiconductor device fabrication equipment of claim 35, wherein the transmitter comprises:

a laser that generates the beam;

a focusing lens positioned to focus the beam; and an oscillating mirror positioned to reflect the beam into the measurement volume.

* * * * *